United States Patent
Moradi et al.

(10) Patent No.: US 10,991,100 B2
(45) Date of Patent: Apr. 27, 2021

(54) DISEASE DETECTION ALGORITHMS TRAINABLE WITH SMALL NUMBER OF POSITIVE SAMPLES

(71) Applicant: INTERNATIONAL BUSINESS MACHINES CORPORATION, Armonk, NY (US)

(72) Inventors: Mehdi Moradi, San Jose, CA (US); Chun Lok Wong, San Jose, CA (US)

(73) Assignee: INTERNATIONAL BUSINESS MACHINES CORPORATION, Armonk, NY (US)

(*) Notice: Subject to any disclaimer, the term of this patent is extended or adjusted under 35 U.S.C. 154(b) by 0 days.

(21) Appl. No.: 16/738,399

(22) Filed: Jan. 9, 2020

(65) Prior Publication Data
US 2020/0151879 A1     May 14, 2020

Related U.S. Application Data

(63) Continuation of application No. 15/697,354, filed on Sep. 6, 2017, now Pat. No. 10,565,708.

(51) Int. Cl.
*G06T 7/00*     (2017.01)
*G06K 9/00*     (2006.01)
(Continued)

(52) U.S. Cl.
CPC ........ *G06T 7/0014* (2013.01); *G06K 9/00127* (2013.01); *G06K 9/6267* (2013.01); *G06N 3/0454* (2013.01); *G06N 3/08* (2013.01); *G06N 20/00* (2019.01); *G06T 7/0012* (2013.01); *G16H 30/40* (2018.01); *G16H 50/20* (2018.01); *G16H 50/70* (2018.01); *G06K 2209/05* (2013.01); *G06N 3/0445* (2013.01);
(Continued)

(58) Field of Classification Search
None
See application file for complete search history.

(56) References Cited

U.S. PATENT DOCUMENTS

2016/0140751 A1    5/2016   Jafarkhani et al.
2016/0174902 A1    6/2016   Georgescu et al.
(Continued)

OTHER PUBLICATIONS

"Atlas-based registration of computed tomography perfusion maps for identification of regional functional deficits," IP.com, IPCOM000231469D, Oct. 1, 2013.
(Continued)

*Primary Examiner* — David Perlman
(74) *Attorney, Agent, or Firm* — Erick Huestis; Stephen Kenny; Foley Hoag, LLC

(57) ABSTRACT

Disease detection from medical images is provided. In various embodiments, a medical image of a patient is read. The medical image is provided to a trained anatomy segmentation network. A feature map is received from the trained anatomy segmentation network. The feature map indicates the location of at least one feature within the medical image. The feature map is provided to a trained classification network. The trained classification network was pre-trained on a plurality of feature map outputs of the segmentation network. A disease detection is received from the trained classification network. The disease detection indicating the presence or absence of a predetermined disease.

20 Claims, 14 Drawing Sheets

(51) Int. Cl.
  G16H 50/20    (2018.01)
  G06N 20/00    (2019.01)
  G06N 3/04     (2006.01)
  G16H 50/70    (2018.01)
  G06K 9/62     (2006.01)
  G06N 3/08     (2006.01)
  G16H 30/40    (2018.01)
  G06N 5/00     (2006.01)
  G06N 20/10    (2019.01)
  G06N 20/20    (2019.01)

(52) U.S. Cl.
  CPC .......... G06N 3/0472 (2013.01); G06N 5/003 (2013.01); G06N 20/10 (2019.01); G06N 20/20 (2019.01); G06T 2207/10081 (2013.01); G06T 2207/20081 (2013.01); G06T 2207/30004 (2013.01); G06T 2207/30048 (2013.01)

(56) References Cited

U.S. PATENT DOCUMENTS

| | | |
|---|---|---|
| 2016/0292856 A1 | 10/2016 | Niemeijer et al. |
| 2017/0032090 A1 | 2/2017 | Kamen et al. |
| 2017/0091528 A1 | 3/2017 | Savvides et al. |
| 2018/0204046 A1* | 7/2018 | Bhattacharya ....... G06K 9/6255 |
| 2018/0276813 A1 | 9/2018 | Gur et al. |
| 2019/0065817 A1 | 2/2019 | Mesmakhosroshahi et al. |

OTHER PUBLICATIONS

"Automated classification of computed tomography axial slices into anatomical region labels," IP.com, Dec. 3, 2014.

"Lesion detection in medical images by cascade classification of bag of boundary features," IP.com, IPCOM000237626D, Jun. 27, 2014.

Cho et al., "How much data is needed to train a medical image deep learning system to achieve necessary high accuracy?," (Jan. 2016).

De Brebisson et al., "Deep neural networks for anatomical brain segmentation," 2015 IEEE Conference on Computer Vision and Pattern Recognition Workshops (2015).

Fei-Fei et al., "One-Shot Learning of Object Categories," IEEE T Pattern Anal, 28(4):594-611 (2006).

Geva et al., "Atrial septal defects," Lancet, 383: 1921-1932 (2014).

Goodfellow et al., "Generative adversarial nets," Adv Neur In, pp. 1-9 (2014).

Kingma et al., "Adam: A method for stochastic optimization," ICLR, pp. 1-15 (2015).

Lai, "Deep learning for medical image segmentation," (Apr. 2015).

Moradi et al., "A hybrid learning approach for semantic labeling of cardiac CT slices and recognition of body position," ISBI, pp. 1418-1421 (2016).

O'Leary et al., "Imaging the pericardium: appearances on ECG-gated 64-detector row cardiac computed tomography," Brit J Radiol, 83(987):194-205 (2010).

Penny et al., "Ventricular septal defect," Lancet, 377:1103-1112 (2011).

Ronneberger et al., "U-net: Convolutional networks for biomedical image segmentation," MICCAI, 234-241 (2015).

Shin et al., "Deep convolutional neural networks for computer-aided detection: CNN architectures, dataset characteristics and transfer learning," IEEE T Med Imaging, 35(5): 1-14 (2016).

Simonyan et al., "Very deep convolutional networks for large-scale image recognition," arXiv, pp. 1-14 (2014).

Socher et al., "Zero-shot learning through cross-modal transfer," Adv Neur In, pp. 1-10 (2013).

* cited by examiner

FIG. 3F Seg n=64
FIG. 3E Seg n=32
FIG. 3D Seg n=16

DISEASE DETECTION ALGORITHMS TRAINABLE WITH SMALL NUMBER OF POSITIVE SAMPLES

CROSS-REFERENCE TO RELATED APPLICATIONS

This application is a continuation of U.S. application Ser. No. 15/697,354, filed Sep. 6, 2017, which is hereby incorporated by reference in its entirety.

BACKGROUND

Embodiments of the present disclosure relate to disease detection from medical images, and more specifically, to disease detection algorithms trainable with small number of positive samples.

BRIEF SUMMARY

According to embodiments of the present disclosure, methods of and computer program products for disease detection from medical images are provided. In various embodiments, a medical image of a patient is read. The medical image is provided to a trained anatomy segmentation network. A feature map is received from the trained anatomy segmentation network. The feature map indicates the location of at least one feature within the medical image. The feature map is provided to a trained classification network. The trained classification network was pre-trained on a plurality of feature map outputs of the segmentation network. A disease detection is received from the trained classification network. The disease detection indicating the presence or absence of a predetermined disease.

According to embodiments of the present disclosure, systems for disease detection from medical images are provided. In various embodiments, the system comprises a data store comprising a plurality of medical images, a trained anatomy segmentation network, a trained disease classification network, and a computing node. The computing node is operable to perform a method comprising: reading a medical image of a patient from the data store; providing the medical image to the trained anatomy segmentation network; receiving from the trained anatomy segmentation network a feature map, the feature map indicating the location of at least one feature within the medical image; providing the feature map to the trained disease classification network; and receiving from the trained classification network a disease detection, the disease detection indicating the presence or absence of a predetermined disease.

BRIEF DESCRIPTION OF THE SEVERAL VIEWS OF THE DRAWINGS

FIGS. 3A-F illustrate exemplary segmentation results for an unseen negative image according to embodiments of the present disclosure.

DETAILED DESCRIPTION

Figure 1:
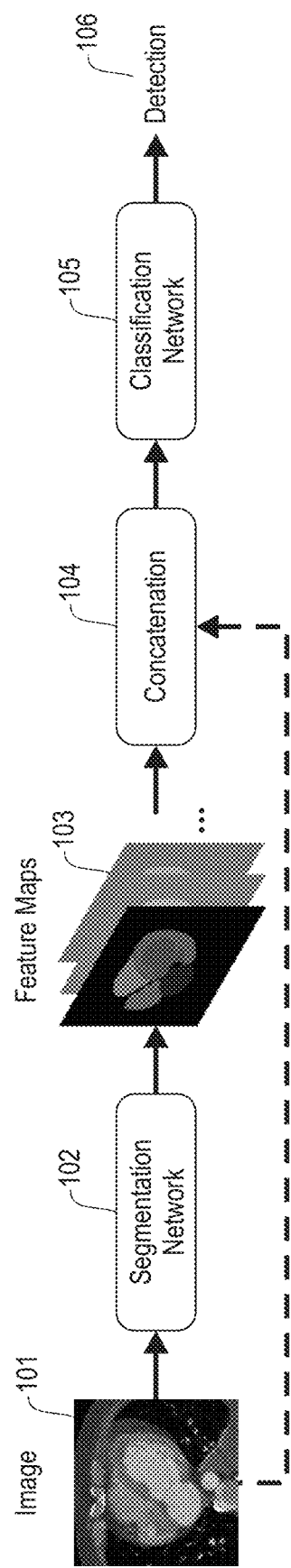
FIG. 1 illustrates a pipeline for disease detection in medical imagery according to embodiments of the present disclosure.

Big data methods may be applied to improve the benchmarks of classification and detection challenges in computer vision. Although deep learning can provide promising results in image analysis, the lack of very large annotated datasets is a barrier to realizing the full potential of such learning systems. The limited number of positive samples for a given detection create unbalanced datasets that limit the true positive rates of trained models.

This issue is particularly acute in medical imaging. Given the large variety of possible clinical conditions in an imaging modality, such as chest computed tomography (CT), it is extremely challenging to build a sufficiently large dataset with representative samples of abnormalities. As a result, most learning-based medical image analysis solutions focus on a narrow range of diseases and have limited practical value. Apart from lack of generality, limited positive samples also create unbalanced datasets. If an unbalanced dataset is directly used to train a classifier, low true positive rates can be expected.

Given the rarity of any individual abnormality in a population, unbalanced datasets are largely unavoidable. Thus, it would be beneficial to extract useful knowledge from negative samples to improve classification accuracy on limited positive samples.

Accordingly, the present disclosure provides for building medical image analysis pipelines that target disease detection. Useful knowledge is extracted from the negative samples and such knowledge is used to improve the classification on limited positive samples.

In various embodiments, a discriminative segmentation model is trained only on normal images to provide a source of knowledge to be transferred to a disease detection classifier. Using the feature maps of a trained segmentation network, deviations from normal anatomy can be learned by a binary convolutional network on an extremely unbalanced training dataset with as little as one positive for 17 negative samples. Although the segmentation network is only trained on normal images, the resulting feature maps can be used to detect pericardial effusion and septal defects on a binary convolutional network.

In various exemplary embodiments, the ratio of positive to negative samples is 1:17. However, it will be appreciated that various ratios of positive to negative samples are enabled by the present disclosure. For example, in some embodiments, the network is trained on a set comprising no more than 10% positive (abnormal) images.

In various embodiments, a fully convolutional segmentation network is used to characterize normal (negative)

anatomy of the heart without seeing any abnormal (positive) samples. Segmentation networks output a label per pixel and thus provide the shapes and locations of the structures of interest. Thus, a trained segmentation network produces useful features for better classification accuracy on unbalanced data. Deviations from normal anatomy can be learned from the feature maps produced by this segmentation network using a binary convolutional network, trained on an extremely unbalanced training dataset with as little as one positive for 17 negative samples.

The approaches provided herein outperform alternative generative models. In particular, simple generative models may not be able to characterize delicate variations that separate normal from disease in medical imaging. Highly complex generative models require very large training sets.

Various advantages outlined herein are attributable to the ability of the segmentation network to transfer image information to semantic pixel level labels provided by experts such as radiologists. Cross-modal knowledge transfer from image to semantic text space can be used to detect unseen objects in new samples. The segmentation network used in various embodiments is optimized for segmentation of normal heart anatomy from four chamber cardiac CT slices. By concatenating the low and high level features from the segmentation network, a classification network can be trained on unbalanced data.

Referring now to FIG. 1, a pipeline for disease detection in medical imagery is illustrated according to various embodiments of the present disclosure, combining a segmentation and a classification network. Medical image 101 is provided to segmentation network 102. Segmentation network 102 generates feature maps 103, which correspond to one or more features appearing in image 101. Feature maps 103 are concatenated 104. Concatenation refers to stacking the feature maps, and in some embodiments the image or other inputs, to form a combined input. In some embodiments, the feature maps are concatenated with the original image 101. The concatenated 104 materials are provided to classification network 105, which outputs a detection 106.

Figure 2:
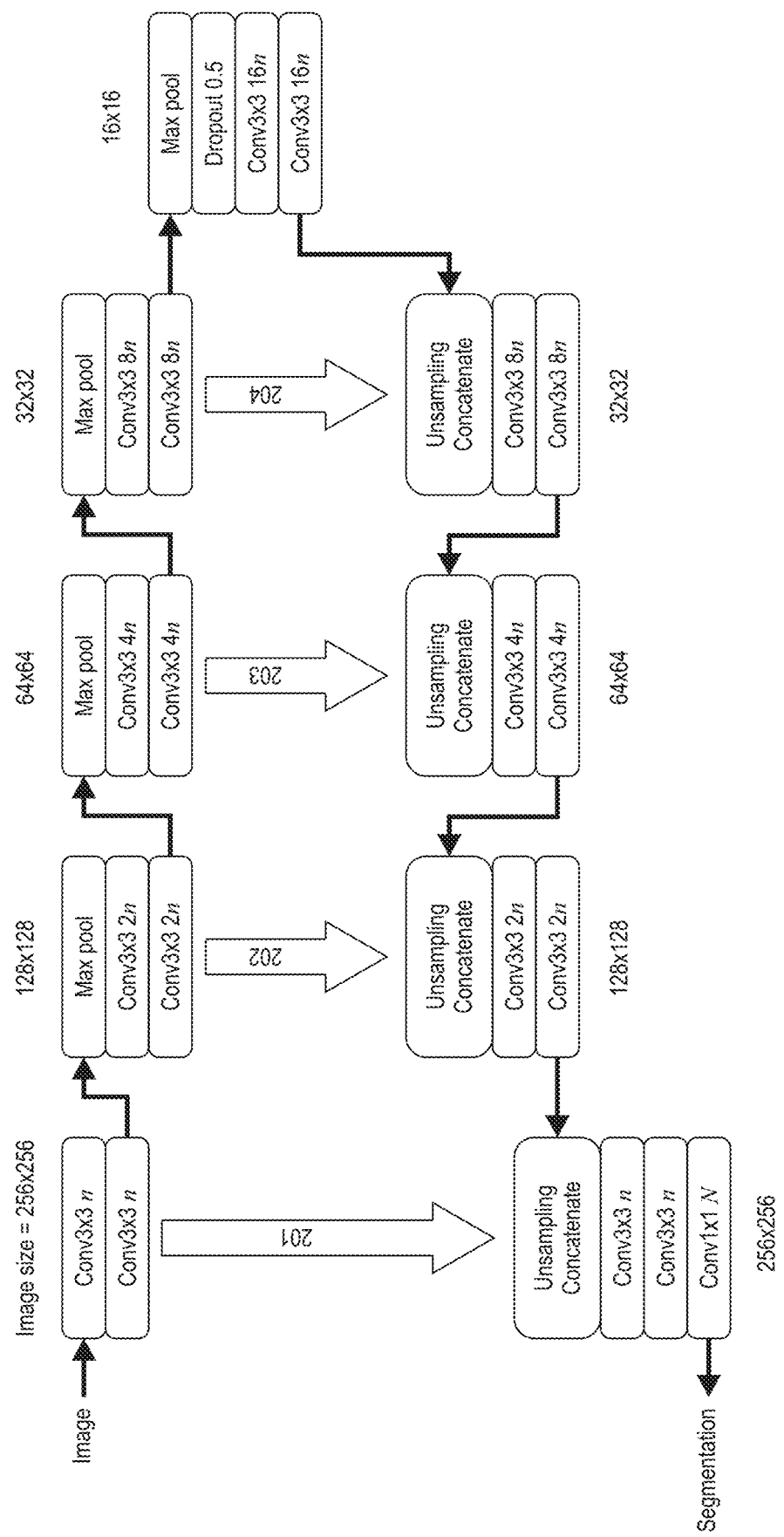
FIG. 2 illustrates an architecture of a segmentation network according to embodiments of the present disclosure.

In various embodiments, segmentation network 102 is a modified version of a fully convolutional architecture, as illustrated with regard to FIG. 2. A convolutional architecture is used because of its capability for accurate segmentation with only a few training samples on biomedical images (e.g., 30 images in). However, it will be appreciated that alternative segmentation networks may be used in accordance with the present disclosure. In various embodiments, classification network 105 is a binary classification network based on the VGGNet architecture. In various embodiments, a separate binary classifier is provided per disease type. Accordingly, a plurality of classification networks 105 are present in various embodiments, although one is pictured for simplicity of explanation.

Referring now to FIG. 2, an architecture of a segmentation network according to various embodiments is illustrated. In FIG. 2, n is the number of feature channels in the first convolution layer, and N is the number of semantic labels.

The contracting path consists of repeated applications of two 3×3 convolutions associated with exponential linear units (ELU), and a 2×2 max pooling. The number of channels is doubled after each pooling. The expanding path consists of 2×2 upsampling by repetition, a concatenation with the correspondingly feature maps from the contracting path, and two ELU-associated 3×3 convolutions that halve the number of channels. Padding is used for each convolution to ensure segmentation image of the same size. A final layer of 1×1 convolution is used to map the feature maps to the number of interested semantic labels. Four max pooling and four upsampling layers are provided. Instead of using 64 channels (n=64) for the first convolution layer, 16 channels (n=16) is used as it provides high accuracy with fewer parameters. Arrows 201 . . . 204 indicate copying of feature maps. The feature maps from the last concatenation layer and the last convolution layer are input as different feature combinations.

For the classification network 105, an architecture with 16 weight layers is used, which consists of 13 3×3 convolution layers followed by three fully-connected layers. A max pooling layer (five in total) is placed for every two or three convolution layers. The last fully-connected layer only has two nodes for binary classification.

During training of the segmentation network, pixel-wise softmax is applied to the output of the last convolution layer to compute the probability maps for the semantic labels. Weighted cross entropy is then used to compute the loss function as in Equation 1, where x is the pixel position and l(x) is the corresponding ground truth label; $p_{l(x)}$ is the softmax probability of the channel corresponds to l(x); $w_{l(x)}$ is the weight computed from the pixel label frequencies of all training atlases as $w_l = 1 - f_l^{1/4}/\Sigma_k f_k^{1/4}$, with $f_k$ the number of pixels of ground truth label k.

$$L = -\sum_x w_{l(x)} \log(p_{l(x)}) \qquad \text{Equation 1}$$

Although the weights are not summed to one, they reduce the influences of more frequently seen labels. The stochastic optimization algorithm Adam is used for fast convergence. The same training process is applied for the classification network, with the summation in Equation 1 removed and l ∈ 0,1. Furthermore, $w_l = 1 - f_l^{1/4}/\Sigma_k f_k^{1/4}$ to avoid over penalty of the negative samples as the ratio of the negative to the positive samples can be large.

For the combined architecture, the segmentation network is trained by the data which are not used by the training and testing of the classification network. In various exemplary embodiments, the system is trained to segment 2D CT slices depicting the four chambers of the heart into five labels: RV, LV, RA, LA, and ventricular myocardium.

Using the trained segmentation network, a variety of feature maps can be obtained that can be used along with the original image for the classification step. Various arrangements of concatenation step 104 are possible, in each case creating a combined input for subsequent steps. A selection of arrangements is compared with using the original image alone for disease/normal classification, as follows. In the IMG arrangement, only the original image is input to the classification network. In the SEG arrangement, the feature maps of the final 1×1 convolution layer (N channels) of the segmentation network are input to the classification network. This provides the high level segmentation feature maps. In the IMG+SEG arrangement, the SEG arrangement is supplemented with the original image. In the CONCAT arrangement, the feature maps from the final upsampling and concatenation layer are input to the classification network. This provides feature maps (3n channels) with both low and high level features. In the IMG+CONCAT arrangement, the CONCAT arrangement is supplemented with the original image.

In an exemplary embodiment, performance on disease detection from cardiac CT data was evaluated as described below. Input images included cases of pericardial effusion and septal defects that were diagnosed by radiologists from axial slices depicting the four-chamber view of the heart. Pericardial effusion is the abnormal accumulation of fluid in the pericardium which can impede cardiac filling. Septal defects are congenital abnormalities caused by malformations of the heart, which allow blood to flow between the left and right blood pools.

To avoid the computational costs of 3D networks, the analysis was performed on 2D slices extracted from the CT data. Various automatic methods may be used for extracting the relevant slice that provides accuracy around 99% in detecting the four chamber view. In the present example, there were 30 2D images for pericardial effusion and 30 2D images for septal defects to provide the positive samples.

For the negative samples, 40 3D CT images from 40 patients without the diseases of interest were used. For each 3D image, six anatomical labels were manually segmented by a radiologist, including the background (BG), right atrium (RA), left atrium (LA), right ventricle (RV), left ventricle (LV), and myocardium (Myo), thus N=6 (referring to FIG. 2). Multiple four-chamber slices are extracted from each case totaling 425 2D images. All positive and negative samples were resized to 256×256 pixels.

Only negative cases were used to train the segmentation network. Four-fold cross validations were performed. For each test, images from 30 patients (~300 2D images) were used for training and the rest (~100 2D images) were used for testing. To validate the segmentation accuracy, the dice coefficients of all six labels between the segmentation and the ground truth were computed. To decide the number of channels for the first convolution layer (n), experiments were performed with n=8, 16, 32, 64. The network was trained with a batch size of 10, 100 batches per epoch, and 20 epochs.

The averaged results of the cross-validations are shown in Table 1. Regardless of the values of n, the backgrounds were accurately segmented. The dice coefficients for other labels were lower but still highly accurate. The worst performance happens when n=8, which had the lowest mean and highest standard deviation. For other values of n, the standard deviations were not higher than 5%, thus the performance was very consistent among the validations. Therefore, n=16 was chosen for the combined architecture as it requires the least parameters.

TABLE 1

|  | BG | RA | LA | RV | LV | $M_{yo}$ |
| --- | --- | --- | --- | --- | --- | --- |
| n = 8 | 96 ± 0% | 83 ± 4% | 71 ± 29% | 82 ± 6% | 72 ± 9% | 75 ± 11% |
| n = 16 | 96 ± 1% | 86 ± 3% | 88 ± 2% | 86 ± 3% | 76 ± 5% | 83 ± 3% |
| n = 32 | 96 ± 1% | 85 ± 4% | 85 ± 4% | 84 ± 5% | 76 ± 5% | 79 ± 4% |
| n = 64 | 96 ± 1% | 85 ± 3% | 86 ± 4% | 86 ± 2% | 77 ± 5% | 82 ± 5% |

Figure 3C:
Figure 3B:
Figure 3A:
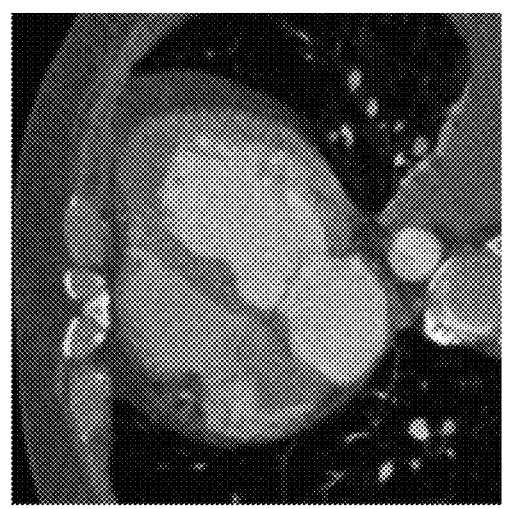

Referring to FIGS. 3A-F, exemplary segmentation results are shown for an unseen negative image. Results with different number of feature channels in the first convolution layer (n) are shown. FIG. 3A is the original image. FIG. 3B is the ground truth segmentation. FIGS. 3C-F show segmentation results with n=8, 16, 32, and 64, respectively. The segmentation is very similar to the ground truth, especially with n=16. Consistent with Table 1, n=8 provided the worst segmentation.

Figure 4B:
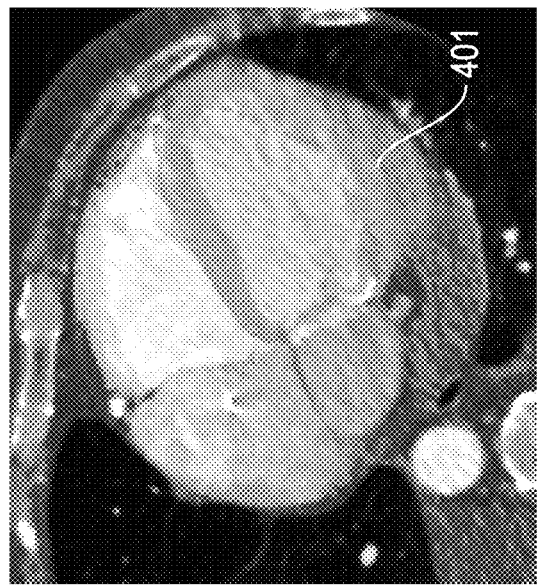
FIGS. 4A-B illustrate exemplary segmentation results for a positive sample of pericardial effusion according to embodiments of the present disclosure.
Figure 4A:
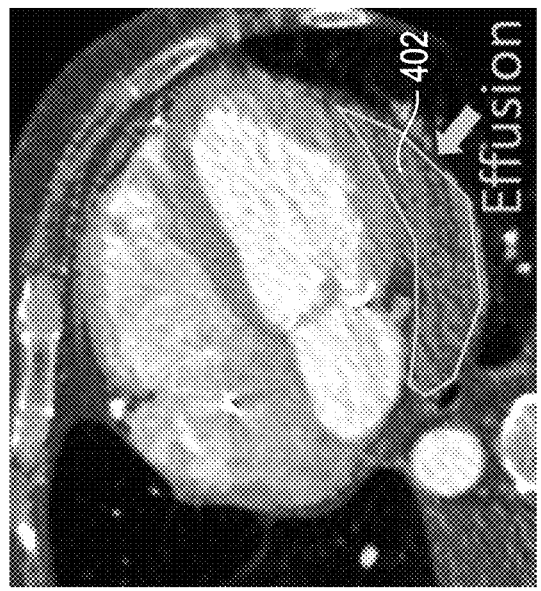

Referring to FIGS. 4A-B, exemplary segmentation results are shown for a positive samples of pericardial effusion. In this example, the myocardium segmentation 401 partially captured the effusion 402.

Figure 5B:
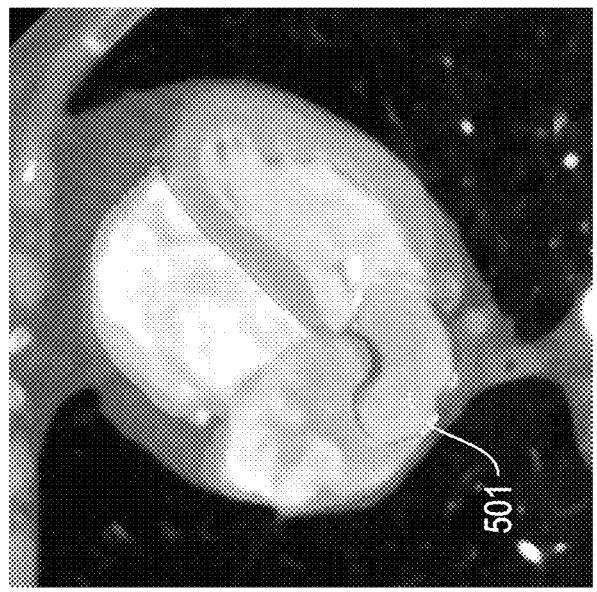
FIG. 5A-B illustrate exemplary segmentation results for a positive sample of septal defect according to embodiments of the present disclosure.
Figure 5A:
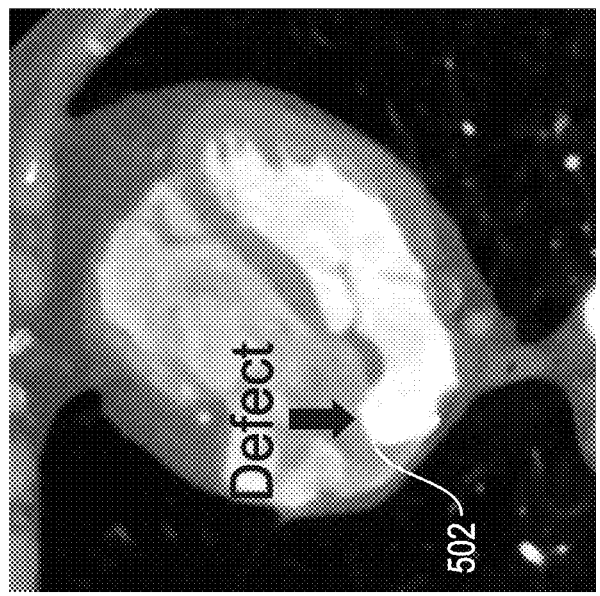

Referring to FIGS. 5A-B, exemplary segmentation results are shown for a positive sample of septal defect. In this example, the right atrium segmentation 501 partially captured the defected shape 502.

It will be apparent from the above examples that the segmentation network can provide useful semantic and shape information for disease detection, without being trained on them.

Figure 6A:
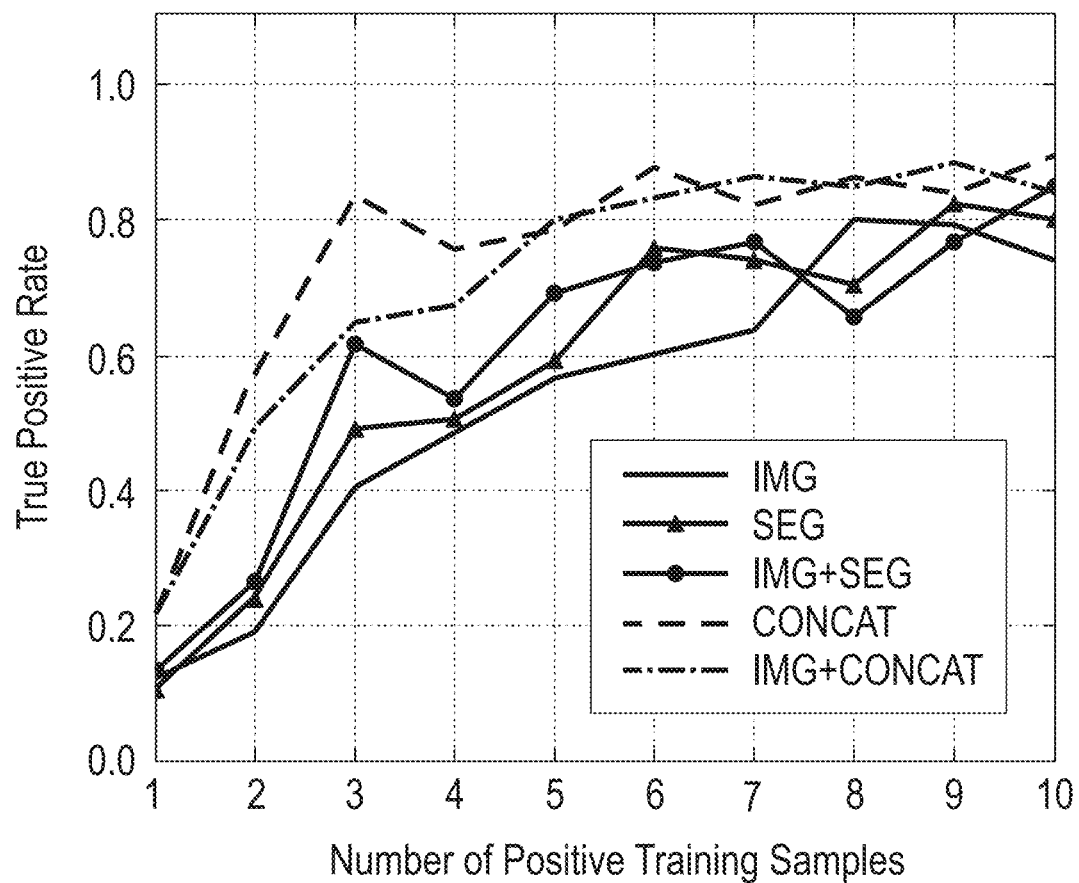
FIGS. 6A-C illustrate the true positive rate, true negative rate, and Cohen's kappa relative to the number of positive training samples for pericardial effusion according to various embodiments of the present disclosure.
Figure 6B:
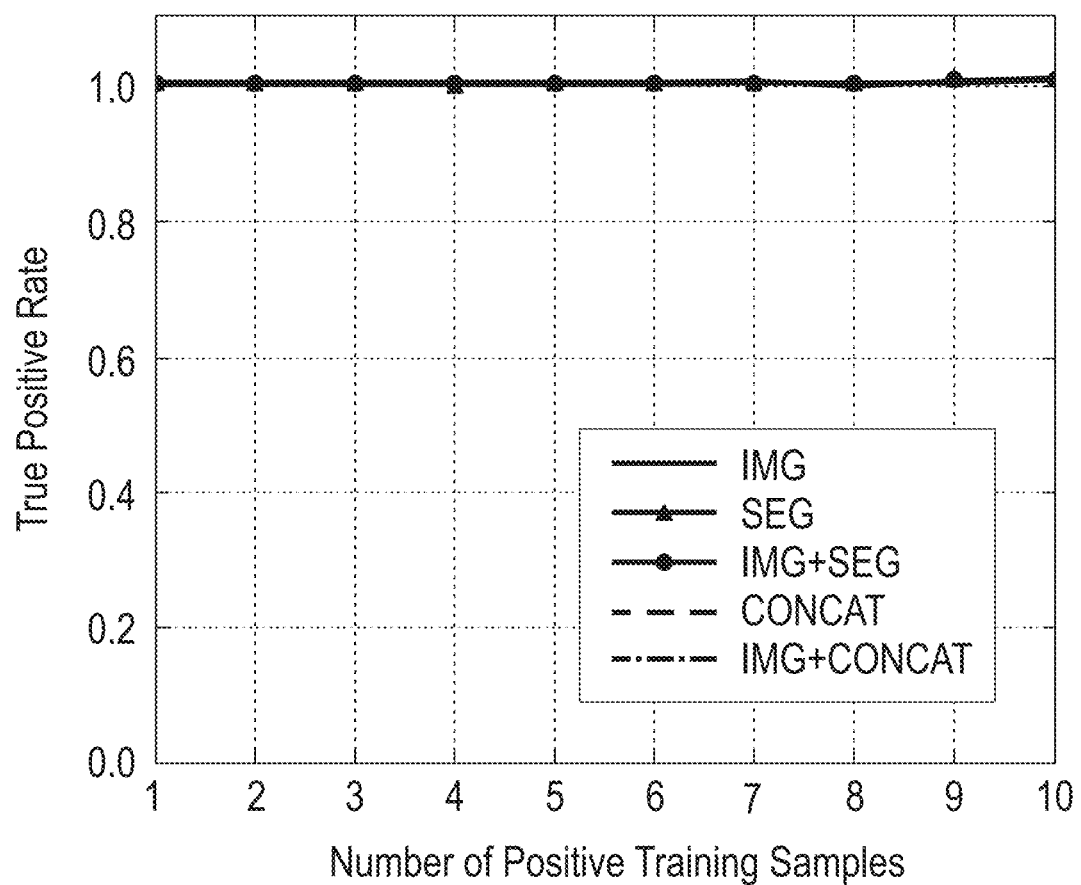
Figure 6C:
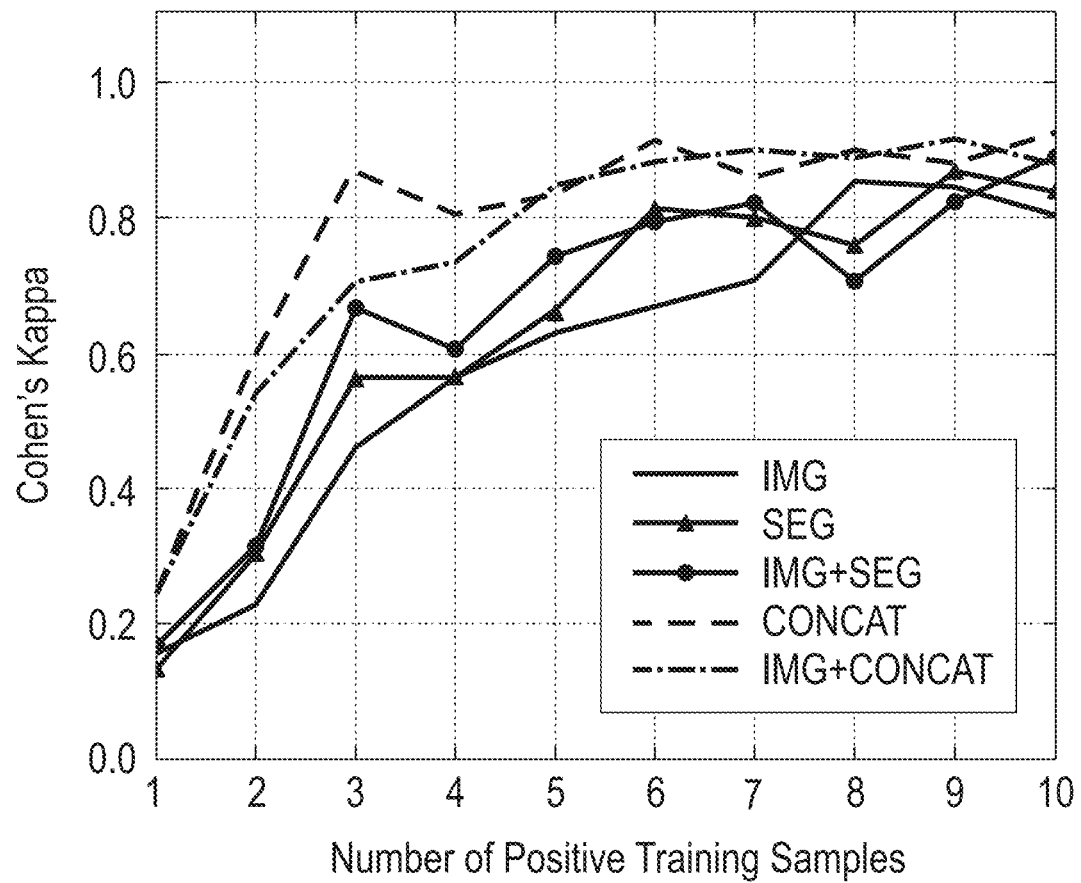
Figure 7A:
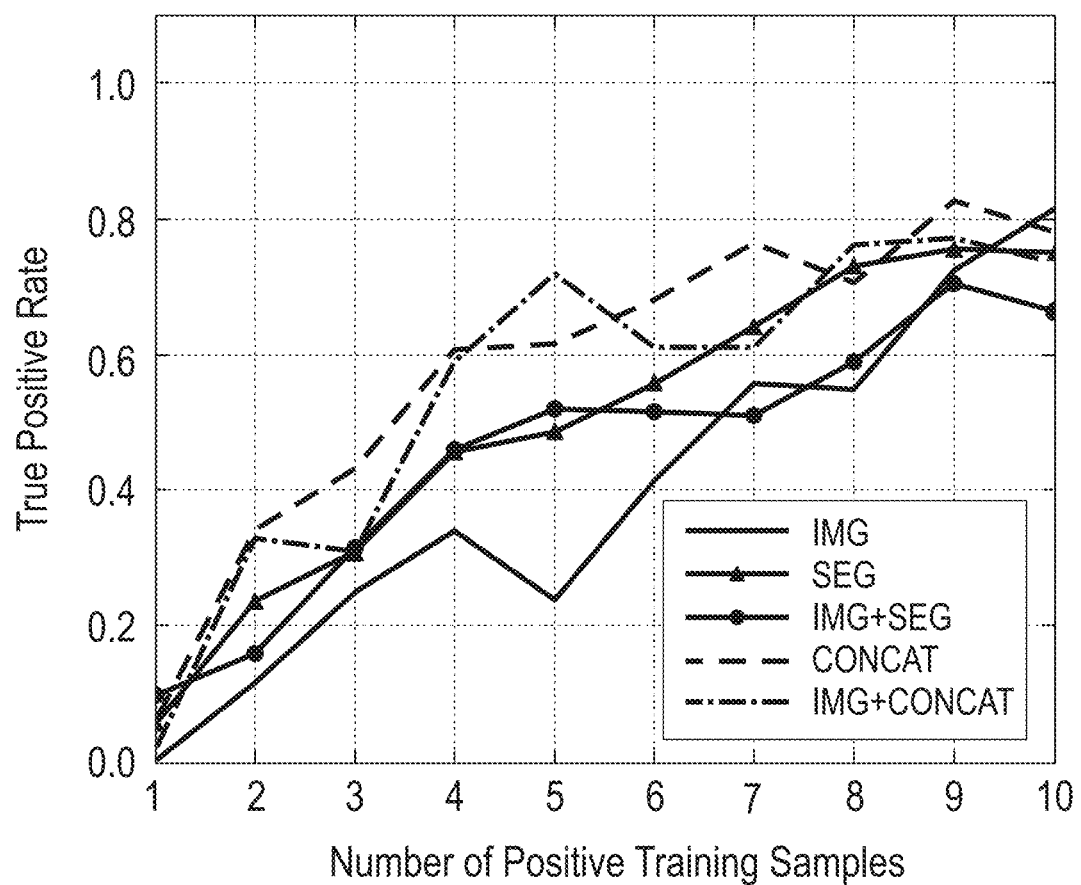
FIGS. 7A-C illustrate the true positive rate, true negative rate, and Cohen's kappa relative to the number of positive training samples for septal defect according to various embodiments of the present disclosure.
Figure 7B:
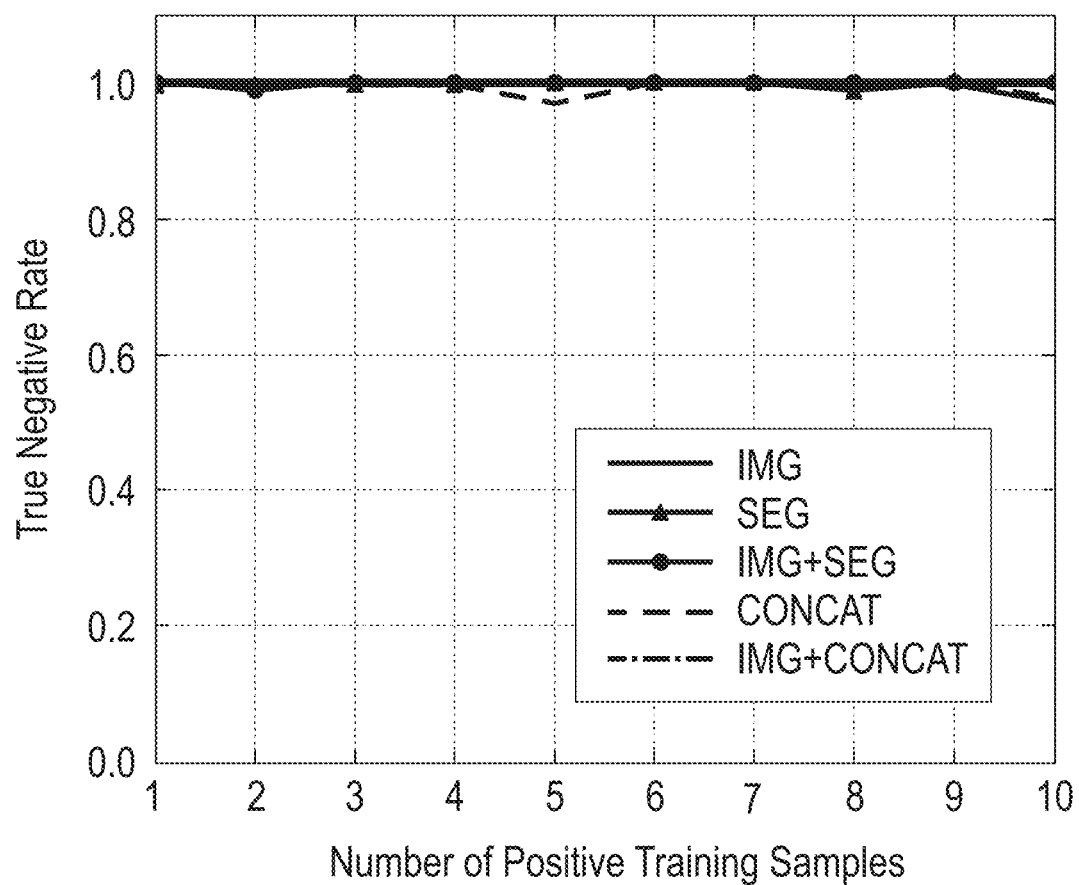
Figure 7C:
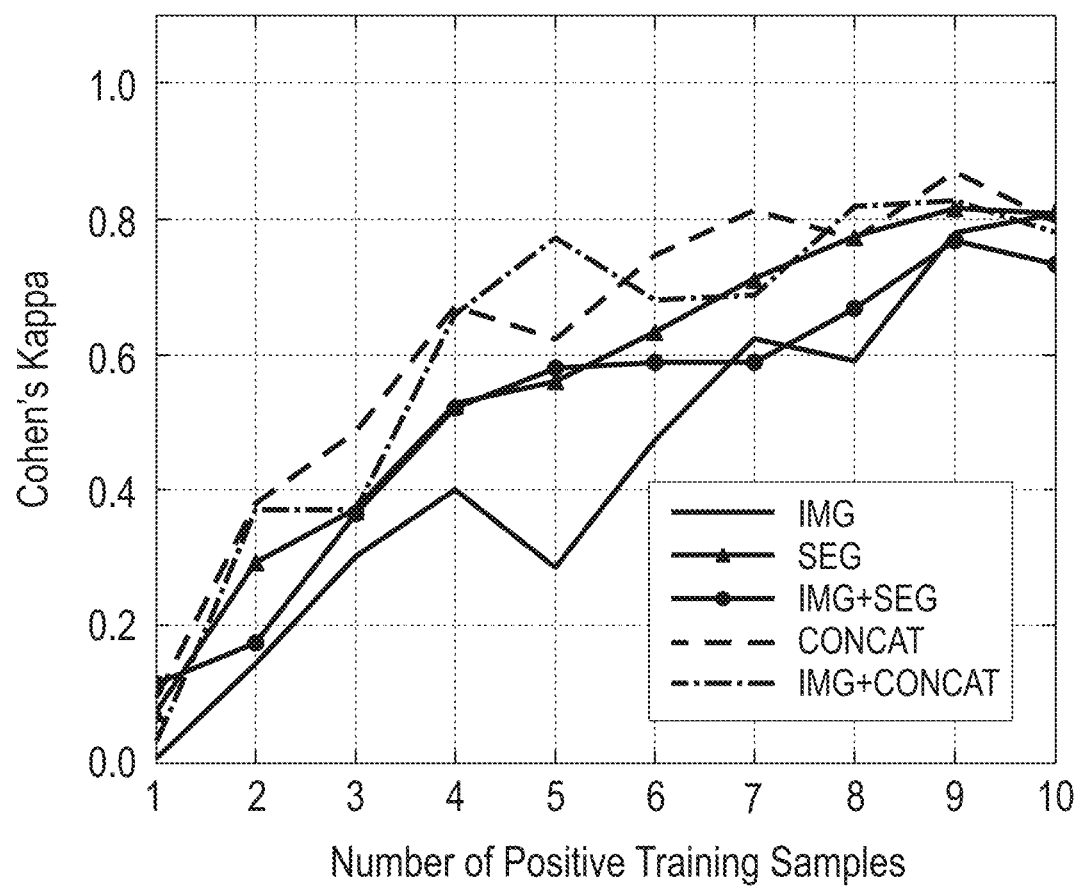

Referring now to FIGS. 6A-C and 7A-C, classification results of different feature combinations with different number of positive training samples are illustrated. The number of negative training samples is 50. The numbers of negative and positive testing samples are 50 and 20, respectively. FIGS. 6A-C are with reference to the detection of pericardial effusion. FIGS. 7A-C are with reference to the detection of septal defect. In each case, the disease classifier is a VGG CNN architecture.

In this example, one of the trained segmentation models (n=16) is used as the source of features, and the corresponding 100 testing images from 10 patients are used as the negative samples. For each test, the negative samples were randomly divided into two equal sized (50) sets for training and testing the classification network. For the 30 positive samples of each disease, they were randomly divided into 10 samples for training and 20 samples for testing. To study the performance with respect to the number of positive samples, ten models were trained with one to ten positive samples. Ten tests were performed for each feature combination for statistical significance. The true positive rate, true negative rate, and Cohen's kappa (as depicted in FIGS. 6 and 7) were used to evaluate the results. Cohen's kappa ($\in$ [−1,1]) provides the inter-rater agreement between the ground truth and detected disease classes. The network was trained with a batch size of 10, 10 batches per epoch, and 20 epochs.

Referring back to FIGS. 6 and 7, the classification performance is shown for pericardial perfusion and septal defect detection, respectively. For both pericardial effusion and septal defect detections, as the number of negative training samples was dominant, the true negative rates were nearly one for any of the feature combinations. The performances can be distinguished by the true positive rate and the Cohen's kappa. When only the original CT slice was used as input (IMG), performance was severely affected by the small number of positive samples. In contrast, when both low and high level features from the segmentation network were included (CONCAT and IMG+CONCAT), the overall performance had a marked increase at the lower number of positive samples compared to IMG.

When only the high level segmentation features were included (SEG and IMG+SEG), the performance beats IMG, but not CONCAT. For both SEG and CONCAT, the addition of the CT slice itself did not have a significant effect on the results. This is especially true for CONCAT as the low level features were already included. Although the performance on pericardial effusion detection was better than on septal defect detection, the differences among different feature combinations were consistent. For pericardial effusion, CONCAT with only three positive training samples, a ratio of 1 to 17 for positive versus negative cases, achieved a mean true positive rate of 83% and Cohen's kappa of 87%, compared to 41% and 46% for IMG. For septal defect, CONCAT trained with seven positive samples yielded a mean true positive rate of 77% and Cohen's kappa of 81%, compared to 56% and 62% for IMG.

Figure 8:
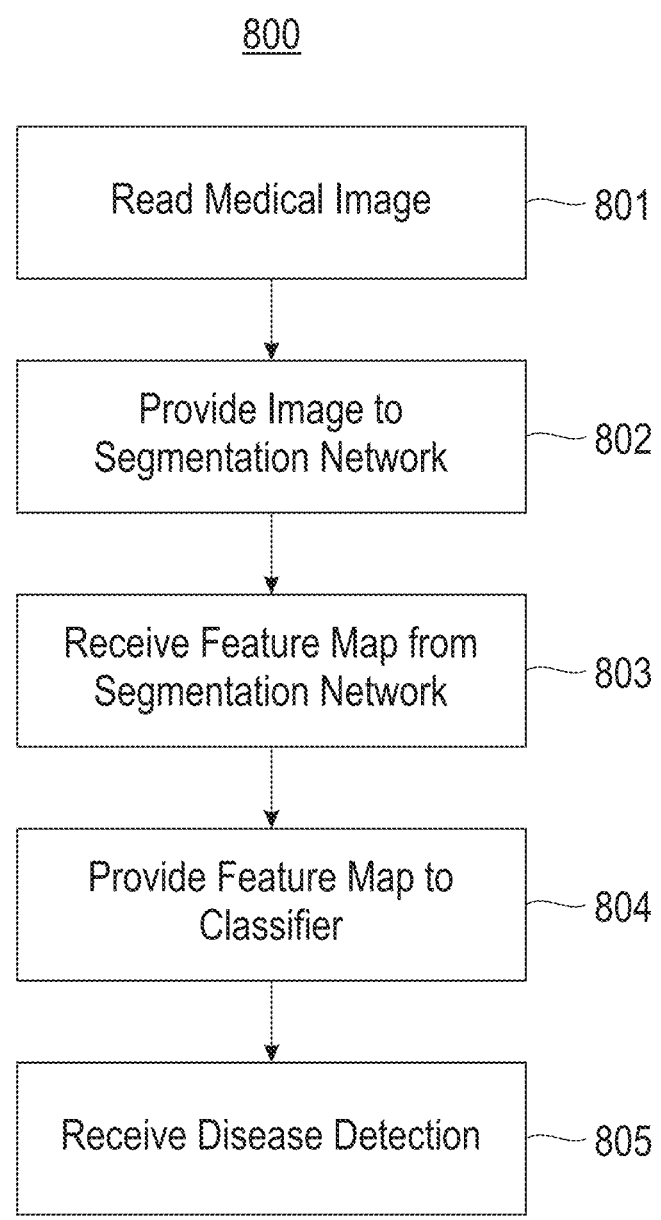
FIG. 8 illustrates a method of disease detection from medical images according to embodiments of the present disclosure.

With reference now to FIG. 8, a method of disease detection from medical images is illustrated. At 801, a medical image of a patient is read. At 802, the medical image is provided to a trained anatomy segmentation network. At 803, a feature map is received from the trained anatomy segmentation network. The feature map indicates the location of at least one feature within the medical image. At 804, the feature map is provided to a trained classification network. The trained classification network was pre-trained on a plurality of feature map outputs of the segmentation network. At 805, a disease detection is received from the trained classification network. The disease detection indicating the presence or absence of a predetermined disease.

As set forth above, frameworks are provided for training a disease detection model with very few positive samples. The use of features from a segmentation network results in accurate disease detection and reduces the number of required positive samples to obtain a given level of accuracy. The segmentation network is trained on normal images only, but produces features for both normal and diseased cases. Significant gains are shown in positive detection rate using these feature maps on a classification network compared to using the original images with the same network. Examples provided herein include cases with two cardiac diseases that are each detected on a different binary classifier. It will be appreciated that the present disclosure is applicable to additional disease types by combining multiple binary classifiers, or by training a multiclass disease detector.

Various embodiments described here in use artificial neural networks, and more particularly convolutional neural networks. However, it will be appreciated that a variety of trainable classifiers are suitable for use according to the present disclosure, including random decision forests, including linear classifiers, support vector machines (SVM), or artificial neural networks (ANN) such as recurrent neural networks (RNN) or convolutional neural network (CNN).

Figure 9:
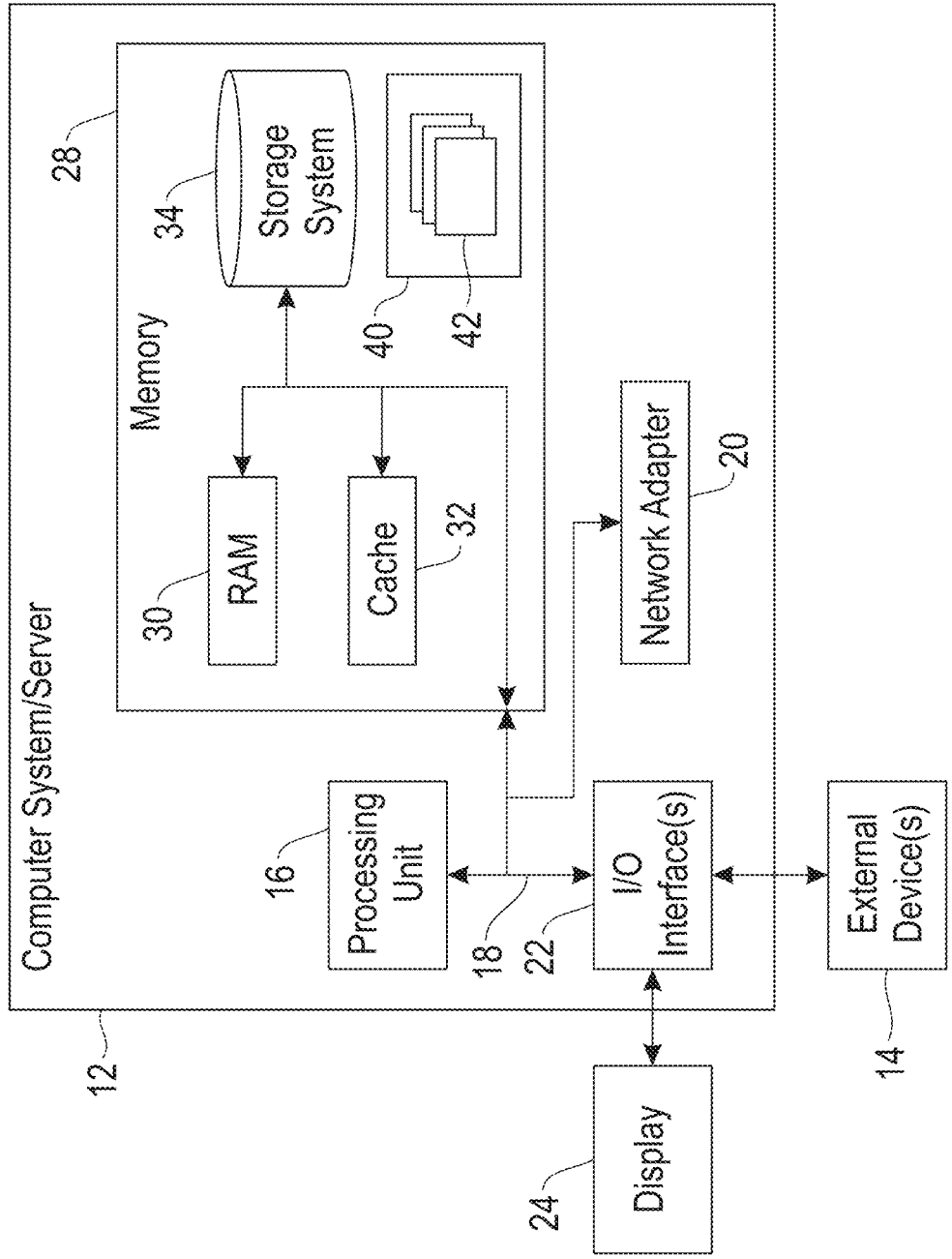
FIG. 9 depicts a computing node according to embodiments of the present disclosure.

Referring now to FIG. 9, a schematic of an example of a computing node is shown. Computing node 10 is only one example of a suitable computing node and is not intended to suggest any limitation as to the scope of use or functionality of embodiments of the invention described herein. Regardless, computing node 10 is capable of being implemented and/or performing any of the functionality set forth hereinabove.

In computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 9, computer system/server 12 in computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method comprising:
reading a medical image of a patient;
providing the medical image to a trained anatomy segmentation network, wherein the trained anatomy segmentation network comprises a plurality of pooling layers followed by a plurality of concatenation layers, each of the plurality of pooling layers and plurality of concatenation layers having associated at least two convolution layers;
receiving from the trained anatomy segmentation network a feature map, the feature map indicating the location of at least one feature within the medical image;
training a classification network using a set of feature maps, each of the set of feature maps being an output of the trained anatomy segmentation network, wherein the set of feature maps comprise feature maps from a last convolution layer of a last concatenation layer;
providing the feature map and the medical image to the trained classification network;
receiving from the trained classification network a disease detection, the disease detection indicating the presence or absence of a predetermined disease.

2. The method of claim 1, further comprising: providing at least one additional feature map to the trained classification network with the medical image.

3. The method of claim 1, wherein the trained anatomy segmentation network comprises a convolutional neural network.

4. The method of claim 1, wherein the trained classification network comprises a convolutional neural network.

5. The method of claim 1, wherein the medical image is a computed tomography image.

6. The method of claim 1, wherein the medical image is a cardiac computed tomography image.

7. The method of claim 1, further comprising:
training the anatomy segmentation network on a set of medical images depicting normal anatomy.

8. The method of claim 1, wherein a majority of the set of feature maps correspond to normal anatomy.

9. A system comprising:
a data store comprising a plurality of medical images;
a trained anatomy segmentation network;
a classification network;
a computing node comprising a computer readable storage medium having program instructions embodied therewith, the program instructions executable by a processor of the computing node to cause the processor to perform a method comprising:
reading a medical image of a patient from the data store;
providing the medical image to the trained anatomy segmentation network,
wherein the trained anatomy segmentation network comprises a plurality of pooling layers followed by a plurality of concatenation layers, each of the plurality of pooling layers and plurality of concatenation layers having associated at least two convolution layers;
receiving from the trained anatomy segmentation network a feature map, the feature map indicating the location of at least one feature within the medical image;
training the classification network using a set of feature maps, each of the set of feature maps being an output of the trained anatomy segmentation network, wherein the set of feature maps comprise feature maps from a last convolution layer of a last concatenation layer;
providing the feature map and the medical image to the trained classification network;
receiving from the trained classification network a disease detection, the disease detection indicating the presence or absence of a predetermined disease.

10. The system of claim 9, the method further comprising:
providing at least one additional feature map to the trained classification network with the medical image.

11. The system of claim 9, wherein the trained anatomy segmentation network comprises a convolutional neural network.

12. The system of claim 9, wherein the classification network comprises a convolutional neural network.

13. The system of claim 9, wherein the medical image is a computed tomography image.

14. The system of claim 9, wherein the medical image is a cardiac computed tomography image.

15. The system of claim 9, the method further comprising:
training the anatomy segmentation network on a set of medical images depicting normal anatomy.

16. The system of claim 9, wherein a majority of the set of feature maps correspond to normal anatomy.

17. A computer program product for disease detection from medical images, the computer program product comprising a computer readable storage medium having program instructions embodied therewith, the program instructions executable by a processor to cause the processor to perform a method comprising:
reading a medical image of a patient;
providing the medical image to a trained anatomy segmentation network, wherein the trained anatomy segmentation network comprises a plurality of pooling layers followed by a plurality of concatenation layers, each of the plurality of pooling layers and plurality of concatenation layers having associated at least two convolution layers;
receiving from the trained anatomy segmentation network a feature map, the feature map indicating the location of at least one feature within the medical image;
training a classification network using a set of feature maps, each of the set of feature maps being an output of the trained anatomy segmentation network, wherein the set of feature maps comprise feature maps from a last convolution layer of a last concatenation layer;
providing the feature map and the medical image to the trained classification network;
receiving from the trained classification network a disease detection, the disease detection indicating the presence or absence of a predetermined disease.

18. The computer program product of claim 17, the method further comprising:
   providing at least one additional feature map to the trained classification network with the medical image.

19. The computer program product of claim 17, wherein the trained anatomy segmentation network comprises a convolutional neural network.

20. The computer program product of claim 17, wherein the trained classification network comprises a convolutional neural network.

\* \* \* \* \*